United States Patent
Nielsen

(10) Patent No.: US 9,670,513 B2
(45) Date of Patent: Jun. 6, 2017

(54) PRODUCTION OF FATTY ACID ALKYL ESTERS

(75) Inventor: Per Munk Nielsen, Hilleroed (DK)

(73) Assignee: NOVOZYMES A/S, Bagsvaerd (DK)

( * ) Notice: Subject to any disclaimer, the term of this patent is extended or adjusted under 35 U.S.C. 154(b) by 714 days.

(21) Appl. No.: 13/979,171

(22) PCT Filed: Jan. 17, 2012

(86) PCT No.: PCT/EP2012/050635
§ 371 (c)(1),
(2), (4) Date: Aug. 28, 2013

(87) PCT Pub. No.: WO2012/098114
PCT Pub. Date: Jul. 26, 2012

(65) Prior Publication Data
US 2015/0353968 A1 Dec. 10, 2015

Related U.S. Application Data

(60) Provisional application No. 61/434,866, filed on Jan. 21, 2011.

(30) Foreign Application Priority Data

Jan. 21, 2011 (EP) .................................... 11151669
Oct. 11, 2011 (EP) .................................... 11184711

(51) Int. Cl.
*C12P 7/64* (2006.01)

(52) U.S. Cl.
CPC ............... *C12P 7/649* (2013.01); *Y02E 50/13* (2013.01)

(58) Field of Classification Search
None
See application file for complete search history.

(56) References Cited

FOREIGN PATENT DOCUMENTS

| WO | 2006/072256 A2 | 7/2006 |
| WO | 2010/049491 A1 | 5/2010 |
| WO | 2012/098114 A1 | 7/2012 |

OTHER PUBLICATIONS

2nd Intl Cong on Biodiesel: Sci Technol, p. 47, No. 29 (2009).
Ghaly et al., American J Biochem Biotechnol, vol. 6, No. 2, pp. 54-76 (2010).
Hong et al., Korean J Chem Engg, vol. 28, No. 9, pp. 1908-1912 (2011).
Ly et al., Process Biochem, vol. 45, pp. 446-450 (2010).
Wantanabe et al., J Am Oil Chem Soc, vol. 84, pp. 1015-1021 (2007).
Guan et al, 2010, Process Biochem, pp. 1677-1682.

*Primary Examiner* — Paul Holland
(74) *Attorney, Agent, or Firm* — Kristin McNamara

(57) ABSTRACT

A method for producing fatty acid alkyl esters, wherein a solution comprising triglyceride, alcohol, water, and glycerol is contacted with a lipolytic enzyme.

20 Claims, 1 Drawing Sheet

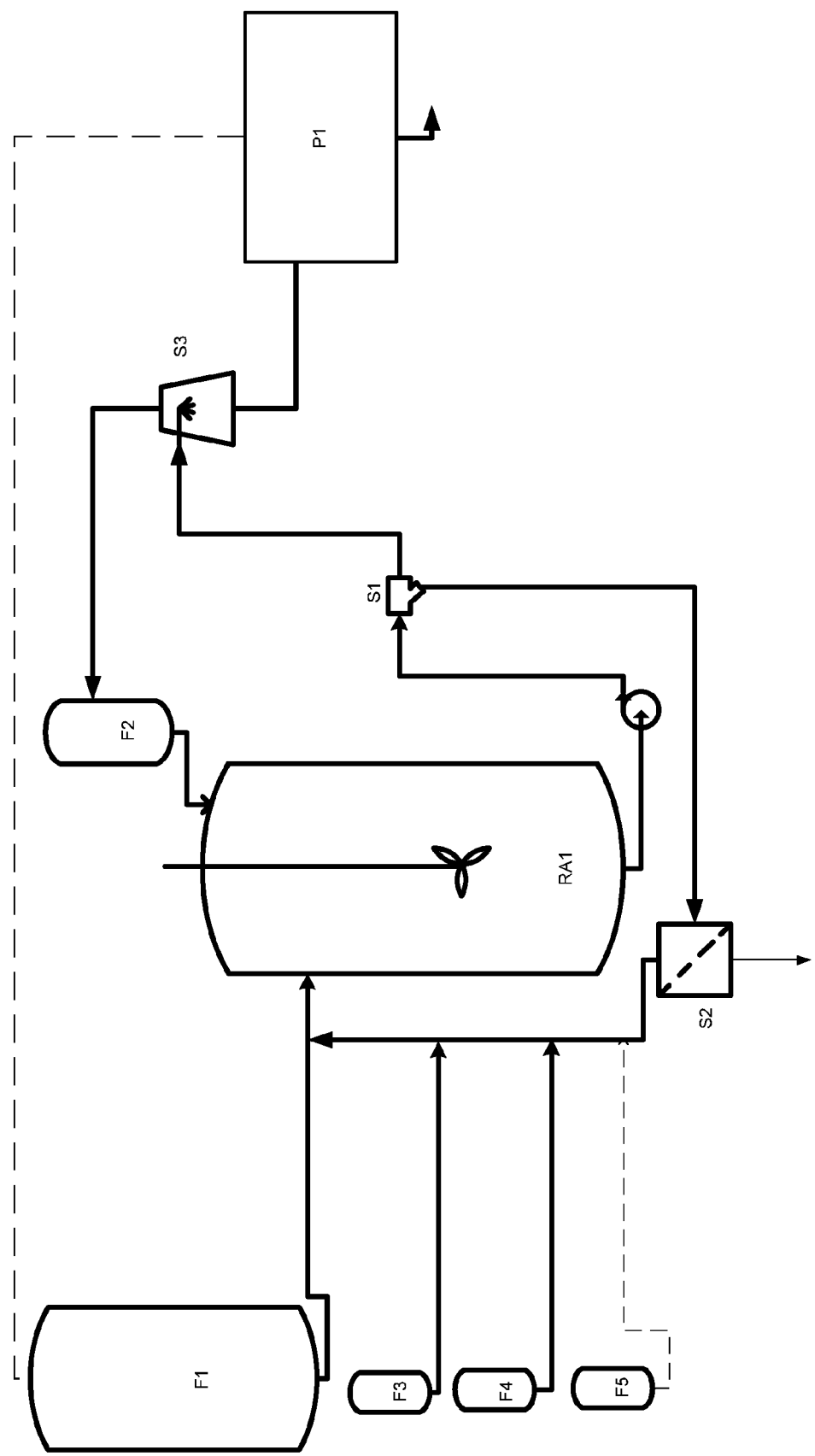

PRODUCTION OF FATTY ACID ALKYL ESTERS

CROSS-REFERENCE TO RELATED APPLICATIONS

This application is a 35 U.S.C. 371 national application of PCT/EP2012/050635 filed Jan. 17, 2012, which claims priority or the benefit under 35 U.S.C. 119 of European application nos. 11151669.6 and 11184711.7 filed Jan. 21, 2011 and Oct. 11, 2011 and U.S. provisional application No. 61/434,866 filed Jan. 21, 2011 the contents of which are fully incorporated herein by reference.

FIELD OF THE INVENTION

The present invention relates to a method for producing fatty acid alkyl esters from fatty acid feedstock.

BACKGROUND ART

Fatty acid alkyl esters may be used as fuel, biodiesel, in standard diesel engines. Biodiesel can be used alone, or blended with fossil diesel. Biodiesel has become more attractive recently because of its environmental benefits.

Although biodiesel is at present primarily produced chemically (using e.g., NaOH and/or sodium methoxide as catalyst), there are several associated problems to restrict its development, such as pre-processing of oil due to high contents of free fatty acids, need for high alcohol surplus in reaction removal of chemical catalyst from ester and glycerol phase, and removal of inorganic salts during glycerol recovery.

The disadvantages caused by chemical catalysts are largely prevented by using lipolytic enzymes as the catalysts and in recent years interest has developed in the use of lipases in transesterification for the production of biodiesel.

Biodiesel produced by enzymatic bioconversion is, compared with chemical conversion, more environmental friendly. However, with very few exceptions, enzyme technology is not currently used in commercial scale biodiesel production.

To make the production of biodiesel economically feasible, the enzyme cost must be as low as possible. This can only be achieved by re-use of the enzyme whether it is an immobilized or a liquid lipase formulation. To be able to use and reuse a liquid enzyme, the enzyme needs to be in the reactant mixture as part of a water phase.

Processes for enzymatic production of fatty acid alkyl esters using liquid enzymes are described in e.g., WO 2006/072256 and Lv et al. (Process Biochemistry 45 (2010) 446-450).

SUMMARY OF THE INVENTION

The inventors of the present invention have now discovered that the transesterification reaction can proceed at a higher rate and/or to a higher percentage of fatty acid alkyl ester and a lower percentage of free fatty acids when part of the water is substituted by glycerol. This is surprising as glycerol is also a reaction product and therefore high glycerol conditions would be expected to slow down the transesterification reaction and/or push the equilibrium of the reaction towards triglyceride formation. It is speculated that the benefit derived from substituted part of the water with glycerol is an effect of the combination of reducing water activity and maintaining a large interface between the glycerol-water phase and the fatty phase. Lipases are interface-active enzymes and thus an increased interface will result in increased substrate availability. At the same time, the reduced water activity will push the reaction towards esterification thereby keeping the amount of free fatty acids low.

A further advantage of maintaining a high volume glycerol-water phase with a lower water content is that less water has to be removed in order to isolate the glycerol from the glycerol-water phase. The liquid lipase and the unreacted alcohol are dissolved in the glycerol-water phase. As the glycerol-water phase is reused in the process, the remaining lipase activity and alcohol is recycled thereby increasing the efficiency of the process.

Accordingly, the present invention relates to a process for production of fatty acid alkyl esters comprising forming a two phase reactant mixture comprising fatty acid feedstock, alcohol, water, and glycerol, contacting the reactant mixture with one or more lipolytic enzyme, wherein the glycerol-water phase constitutes from 5 to 50%, 10 to 50%, 20 to 50%, 20 to 45%, or even 20 to 40% of the reactant mixture (w/w), and, wherein glycerol constitutes 30 to 85%, 40 to 85%, 45 to 85%, 50 to 85% or even 60 to 80% of the glycerol-water phase (w/w).

BRIEF DESCRIPTION OF THE FIGURES

FIG. 1 shows an embodiment of a process of the invention. The FIGURE has been included for illustration purposes alone and should in no way be construed as limiting the invention.

The FIGURE shows a process flow sheet for a batch operation plant. The plant can be constructed also as a continuous stirred tank reactor system.

Feedstock Tanks:
F1: Triglyceride
F2: Alcohol
F3: Lipase
F4: Water
F5: Glycerol (may be added in the first batch)
Reactors:
RA1: Transesterification/esterification reactor. Outlet is a mixture between FAAE and glycerol+water phase to be separated in S1.
Separation Units:
S1: Separation of glycerol/water phase from the mixture out of RA1
S2: Eliminate by separation an amount of glycerol and/or water. This can be either by bleeding off the required volume or by ultrafiltration. S2 is optional as the whole glycerol+water phase may be re-used.
S3: Recovery of alcohol from the FAAE by evaporation.
Process:
P1: Process for elimination of FFA in the FAAE:
   a) caustic wash (recover the FFA and return to F1 after acidification, dotted line)
   b) Esterifying in a process using immobilized lipase by adding dry alcohol (FFA is converted to FAAE, dotted line does not apply)

DETAILED DESCRIPTION OF THE INVENTION

Definitions

Biodiesel:
Fatty acid alkyl esters (FAAE) of short-chain alcohols, such as fatty acid methyl esters (FAME) and fatty acid ethyl esters (FAEE) are also called biodiesel, because they are used as an additive to or as replacement of fossil diesel.

Alcohol:

The alcohol used in the method of the invention is preferably a short-chain alcohol having 1 to 5 carbon atoms ($C_1$, $C_2$, $C_3$, $C_4$, or $C_5$). Preferred alcohols are methanol and ethanol. The alcohol content is preferably less than 4, 3, 2, 1.5 or 1.0 molar equivalents to the amount of fatty acids in the reactant mixture (free and glyceride bound fatty acids). The alcohol may be added stepwise (such as in 1, 2, 3, 4, 5, 6, 7, 8, 9, 10 or more steps) and/or continuously.

Fatty Acid Feedstock:

The term "fatty acid feedstock" is defined herein as a substrate comprising triglyceride. In addition to triglyceride, the substrate may comprise diglyceride, monoglyceride, free fatty acid or any combination thereof. Any oils and fats of vegetable or animal origin comprising fatty acids may be used as substrate for producing fatty acid alkyl esters in the process of the invention.

The fatty acid feedstock may be oil selected from the group consisting of: algae oil, castor oil, coconut oil (copra oil), corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, and oil from halophytes, or any combination thereof.

The fatty acid feedstock may be fat selected from the group consisting of: animal fat, including tallow from pigs, beef and sheep, lard, chicken fat, fish oil, or any combination thereof.

The fatty acid feedstock may be crude, refined, bleached, deodorized, degummed, or any combination thereof.

Food quality oils and fats are expensive and therefore waste and by-products from their processing as well as non-food grade oils and fats have become increasingly attractive feedstock for fatty acid alkyl ester. Soap stock is the fraction of oil obtained in an oil refinery by treating the oil with a base to convert free fatty acids to soaps (e.g., sodium soaps). The soap stock usually contains a fraction of glycerides beside the soaps. Acid oil is the by-product from the oil refinery produced by acidification of soap stock to solubilize the soaps. It mainly contains free fatty acids (FFA) and acylglycerols. Distillates like Palm Fatty Acid Distillate (PFAD) is the by-product from oil refining coming from a distillation process used to eliminate free fatty acid from the oil.

The feedstock may be an intermediate product, a waste product or a by-product of oil or fat refining selected from the group consisting of: soap stock; acid oil; fatty acid distillates such as PFAD, soy fatty acid distillate, rapeseed fatty acid distillate, rice bran fatty acid distillate, poultry fat fatty acid distillate, beef tallow fatty acid distillate, etc.; gums from degumming; by-products from the production of omega-3 fatty acids derivates from fish oil; fat trap grease; yellow grease, and brown grease, free fatty acids like oleic acid; or fractions of oil obtained by physical separations; or any combinations thereof.

Glycerol-Water Phase:

The glycerol-water phase in % of the reactant mixture is defined as (glycerol+water)/(glycerol+water+tri-, di and mono-glyceride+FAAE+FFA) in % (w/w).

The alcohol will be dissolved in both the glycerol-water phase and in the fatty phase with the largest part dissolved in the glycerol-water phase. The alcohol amount is excluded in the calculation of "the glycerol-water phase in % of the reactant mixture".

In the present invention, the glycerol-water phase constitutes from 5 to 50%, 10 to 50%, 20 to 50%, 20 to 45%, or even 20 to 40% of the reactant mixture (w/w). In the glycerol-water phase, glycerol constitutes 30 to 70%, 35 to 70%, 40 to 70% or even 45 to 70% (w/w) or 30 to 85%, 40 to 85%, 45 to 85%, 50 to 85% or even 60 to 80% (w/w).

Lipolytic Enzyme

The one or more lipolytic enzyme applied in the method of the present invention is selected from lipases, phospholipases, cutinases, acyltransferases or a mixture of one and more of lipase, phospholipase, cutinase and acyltransferase. The one or more lipolytic enzyme is selected from the enzymes in EC 3.1.1, EC 3.1.4, and EC 2.3. The one or more lipolytic enzyme may also be a mixture of one or more lipases. The one or more lipolytic enzyme may include a lipase and a phospholipase. The one or more lipolytic enzyme includes a lipase of EC 3.1.1.3. The one or more lipolytic enzyme includes a lipase having activity on tri-, di-, and monoglycerides.

Lipases:

A suitable lipolytic enzyme may be a polypeptide having lipase activity, e.g., one selected from the *Candida antarctica* lipase A (CALA) as disclosed in WO 88/02775, the *C. antarctica* lipase B (CALB) as disclosed in WO 88/02775 and shown in SEQ ID NO:1 of WO2008065060, the *Thermomyces lanuginosus* (previously *Humicola lanuginosus*) lipase disclosed in EP 258 068), the *Thermomyces lanuginosus* variants disclosed in WO 2000/60063 or WO 1995/22615, in particular the lipase shown in positions 1-269 of Sequence Number 2 of WO 95/22615, the *Hyphozyma* sp. lipase (WO 98/018912), and the *Rhizomucor miehei* lipase (Sequence Number 5 in WO 2004/099400), a lipase from *P. alcaligenes* or *P. pseudoalcaligenes* (EP 218 272), *P. cepacia* (EP 331 376), *P. glumae*, *P. stutzeri* (GB 1,372,034), *P. fluorescens*, *Pseudomonas* sp. strain SD 705 (WO 95/06720 and WO 96/27002), *P. wisconsinensis* (WO 96/12012); a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Also preferred is a lipase from any of the following organisms: *Fusarium oxysporum, Absidia reflexa, Absidia corymbefera, Rhizomucor miehei, Rhizopus delemar (oryzae), Aspergillus niger, Aspergillus tubingensis, Fusarium heterosporum, Aspergillus oryzae, Penicilium camembertii, Aspergillus foetidus, Aspergillus niger, Aspergillus oryzae* and *Thermomyces lanuginosus*, such as a lipase selected from any of Sequence Numbers 1 to 15 in WO 2004/099400.

A preferred lipase for use in the present invention is a lipase having a sequence identity to the mature polypeptide of Sequence Number 2 of at least a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100% sequence identity to the polypeptide shown in positions 1-269 of Sequence Number 2 of WO 95/22615 or to the polypeptide shown in Sequence Number 1 of WO2008/065060.

Commercial lipase preparations suitable for use in the process of the invention include LIPOZYME CALB L, LIPOZYME® TL 100L and CALLERA™ TRANS (all available from Novozymes A/S).

Phospholipases:

The one or more lipolytic enzyme may include a polypeptide having phospholipase activity, preferably phospholipase $A_1$, phospholipase $A_2$, phospholipase B, phospholipase C, phospholipase D, lyso-phospholipases activity, and/ or any combination thereof. In the process of the invention the one or more lipolytic enzyme may be a phospholipase, e.g., a single phospholipase such as $A_1$, $A_2$, B, C, or D; two or more phospholipases, e.g., two phospholipases, including, without limitation, both type A and B; both type $A_1$ and $A_2$; both type $A_1$ and B; both type $A_2$ and B; both type $A_1$ and C; both type $A_2$ and C; or two or more different phospholipases of the same type.

The one or more lipolytic enzyme may be a polypeptide having phospholipase activity, as well as having acyltransferase activity, e.g., a polypeptide selected from the polypeptides disclosed in WO 2003/100044, WO 2004/064537, WO 2005/066347, WO 2008/019069, WO 2009/002480, and WO 2009/081094. Acyltransferase activity may be e.g., determined by the assays described in WO 2004/064537.

The phospholipase may be selected from the polypeptides disclosed in WO 2008/036863 and WO 20003/2758. Suitable phospholipase preparations are PURIFINE® (available from Verenium) and LECITASE® ULTRA (available from Novozymes A/S). An enzyme having acyltransferase activity is available as the commercial enzyme preparation LYSOMAX® OIL (available from Danisco A/S).

Cutinases:

The one or more lipolytic enzyme may include a polypeptide having cutinase activity. The cutinase may e.g., be selected from the polypeptides disclosed in WO 2001/92502, in particular the *Humicola insolens* cutinase variants disclosed in Example 2.

Preferably, the one or more lipolytic enzyme is an enzyme having at least 60%, at least 70%, at least 80%, at least 90%, at least 95%, at least 96%, at least 97%, at least 98%, or even at least 99% identity to any of the aforementioned lipases, phospholipases, cutinases, and acyltransferases.

In a preferred embodiment, the one or more lipolytic enzyme has at least 60%, at least 70%, at least 80%, at least 90%, at least 95%, at least 96%, at least 97%, at least 98%, at least or even at least 99% identity to the amino acid sequence shown as positions 1-269 of Sequence Number 2 of WO 95/22615.

Enzyme Sources and Formulation:

The one or more lipolytic enzyme used in the process of the invention may be derived or obtainable from any of the sources mentioned herein. The term "derived" means in this context that the enzyme may have been isolated from an organism where it is present natively, i.e. the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g., having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "derived" includes enzymes produced synthetically by e.g., peptide synthesis. The term "derived" also encompasses enzymes which have been modified e.g., by glycosylation, phosphorylation etc., whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g., peptide synthesis. With respect to recombinantly produced enzyme the terms "obtainable" and "derived" refers to the identity of the enzyme and not the identity of the host organism in which it is produced recombinantly.

Accordingly, the one or more lipolytic enzyme may be obtained from a microorganism by use of any suitable technique. For instance, an enzyme preparation may be obtained by fermentation of a suitable microorganism and subsequent isolation of an enzyme preparation from the resulting fermented broth or microorganism by methods known in the art. The enzyme may also be obtained by use of recombinant DNA techniques. Such method normally comprises cultivation of a host cell transformed with a recombinant DNA vector comprising a DNA sequence encoding the enzyme in question and the DNA sequence being operationally linked with an appropriate expression signal such that it is capable of expressing the enzyme in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

The one or more lipolytic enzyme may be applied in any suitable formulation, e.g., as lyophilised powder or in aqueous solution.

Sequence Identity:

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Process Design

Further, the invention relates to a batch process and/or a continuous, staged process to produce fatty acid alkyl esters including processes wherein glycerol and/or water are reused. As the enzymes are in the glycerol-water phase, this phase can be separated from the fatty phase by a decanter, a coalesce, a cyclone or vortex separator, a settler or by centrifugation for reuse of the enzymes. In the continuously process the two phases, fatty phase and glycerol-water phase, respectively, can be processed counter-currently. Kosugi et al. (1990), Biotechnology and Bioengineering, vol. 36, 617-622, describes a continuous, counter-current process to hydrolyse vegetable oil by immobilized lipase. In an embodiment the two phases in the reactant mixture are mixed using a high shear mixer or a cavitator.

During processing, the amount of glycerol may increase to above the optimal level in the glycerol-water phase. Therefore, it may be advantageous to separate the glycerol-water phase or at least a part thereof from the phase comprising the fatty acid alkyl esters, and reduce the amount of glycerol in the glycerol-water phase, e.g., by ultrafiltration, before the phase is reused e.g., in the process of the invention.

The phase comprising the fatty acid alkyl esters may be treated with an alkaline agent, preferably NaOH or KOH, to facilitate the isolation of a soap stock fraction containing FFA. This fraction containing FFA may be acidified (e.g., with HCl or $H_2SO_4$), and the FFA used as raw material in an esterification process, e.g., in the process of the invention.

The fatty phase containing the fatty acid alkyl esters and FFA can be reacted in low water reaction conditions with immobilized lipase with a surplus of dry alcohol. This method use for instance immobilized lipase (e.g. NOVOZYM 435) in a packed bed column or in a stirred tank. The reaction will proceed until equilibrium determined by the amount of water in the reaction. Water is produced by the esterification of free fatty acids. It might be needed to perform the esterification process with the immobilized enzyme in more than one step dependent upon the concentration of free fatty acids in the fatty phase before the reaction and the concentration of FFA acceptable in the end product.

In a preferred embodiment of the process of the invention, soybean oil and methanol is processed to yield FAME using a liquid lipase from *T. lanuginosus*. The glycerol-water phase may comprise 45-85% glycerol and the glycerol-water phase in % of the reactant mixture may be 15-25%. As the soybean oil is degraded and FAME is produced the amount of glycerol increases in the glycerol-water phase. The glycerol-water phase which contains the enzyme and the major fraction of un-reacted methanol may be separated from the FAME phase and re-used for the next batch of triglyceride. Fresh liquid lipase may be added to maintain the lipase activity at the desired level and methanol added to keep the concentration at approximately 1.5 molar equivalents. This embodiment provides a very simple process where most excess methanol and the remaining enzyme activity is recovered with the glycerol-water phase and easily re-used for the next batch. The number of batches is only limited by the volume increase of the glycerol-water phase after each batch and the resulting decrease in fatty phase volume.

The fatty phase (FAME+FFA) from this reaction may be isolated and washed with a NaOH solution to form soap from FFA, where after the soaps are isolated, acidified, separated to collect the FFA which are added back into the process. Alternatively to the alkaline treatment to eliminate FFA, they can be esterified by using a liquid or an immobilized lipase in a separate step.

In another preferred embodiment of the process of the invention, soybean oil and methanol is processed to yield FAME using a liquid lipase from *T. lanuginosus*. The glycerol-water phase comprises 45-85% glycerol and the glycerol-water phase in % of the reactant mixture may be 15-25%. As the soybean oil is degraded and FAME is produced the amount of glycerol increases in the glycerol-water phase. The glycerol-water phase which contains the enzyme and the major fraction of un-reacted methanol is separated from the FAME phase and re-used for the next batch of triglyceride. Part of the glycerol-water phase is removed by separation (bleeding off). When returning the glycerol-water phase to the reactor fresh liquid lipase may be added to maintain the lipase activity at the desired level and methanol may be added to keep the concentration at approximately 1.5 molar equivalents. This embodiment allows processing at equal capacity batch after batch as the volume of glycerol-water phase is kept constant.

The fatty phase (FAME+FFA) from this reaction may be isolated and washed with a NaOH solution to form soap, the soaps are isolated, acidified, separated to collect the FFA which are added back into the process. Alternatively to the alkaline treatment, the FFA can be esterified using a liquid or an immobilized lipase in a separate step.

In another preferred embodiment of the process of the invention, soybean oil and methanol is processed to yield FAME using a liquid lipase from *T. lanuginosus*. The glycerol-water phase comprises 45-85% glycerol and the glycerol-water phase in % of the reactant mixture may be 15-25%. As the soybean oil is degraded and FAME is produced the amount of glycerol increases in the glycerol-water phase. The glycerol-water phase which contains the enzyme and the major fraction of un-reacted methanol is separated from the FAME phase and re-used for the next batch of triglyceride. Part of the glycerol-water phase is removed by separation (bleeding off). Before re-use the glycerol-water phase is separated by gravity to obtain a light fraction and a heavy fraction. The light fraction will have a relatively high enzyme activity. A part of the heavy fraction is removed to reduce the total volume of glycerol-water phase. When returning the glycerol-water phase to the reactor fresh liquid lipase is added to maintain the lipase activity at the desired level and methanol is added to keep the concentration at approximately 1.5 molar equivalents.

The fatty phase (FAME+FFA) from this reaction may be isolated and washed with a NaOH solution to form soap, the soaps are isolated, acidified, separated to collect the FFA which are added back into the process. Alternatively to the alkaline treatment, the FFA can be esterified by using a liquid or an immobilized lipase in a separate step.

In another preferred embodiment of the process of the invention, soybean oil and methanol is processed to yield FAME using a liquid lipase from *T. lanuginosus*. The glycerol-water phase comprises 45-85% glycerol and the glycerol-water phase in % of the reactant mixture may be 15-25%. As the soybean oil is degraded and FAME is produced the amount of glycerol increases in the glycerol-water phase. The glycerol-water phase containing the enzyme and the major fraction of un-reacted methanol is separated from the FAME phase and re-used for the next batch of triglyceride. Part of the glycerol-water phase is removed by separation (bleeding off). Before re-use the glycerol-water phase is separated by ultrafiltration to obtain a retentate fraction comprising the enzyme and a permeate fraction. The permeate fraction is removed to reduce the total volume of glycerol-water phase. When returning the retentate to the reactor fresh liquid lipase, and methanol is added to maintain the lipase activity and the methanol content at the desired level. Water and/and glycerol may be added to adjust the volume of the glycerol-water phase. This embodiment provides a method where almost all the enzyme is recovered from the glycerol-water phase and the volume and composition of the glycerol-water phase in each batch can be kept constant.

The fatty phase (FAME+FFA) from this reaction may be isolated and washed with a NaOH solution to form soap, the soaps are isolated, acidified, separated to collect the FFA which are added back into the process. Alternatively to the alkaline treatment to eliminate FFA, they can be esterified by using a liquid or an immobilized lipase in a separate step.

Fatty Acid Alkyl Ester Composition and its Uses

Fatty acid alkyl esters are used in an extensive range of products and as synthetic intermediates. Some of their industrial applications include use as lubricants, plasticizers, antirust agents, drilling and cutting oils, and starting materials for synthesis of superamides and fatty alcohols. Certain embodiments of the present invention in particular relates to fuels. Fatty acid alkyl esters of short-chain alcohols are non-toxic, biodegradable and an excellent replacement wholly or partly for petroleum based fuel due to the similarity in cetane number, energy content, viscosity and phase changes to those of petroleum based fuels.

A composition produced by the process of the present invention may consist of a mixture of at least two or even three of the following components: FAAE; triglyceride; diglyceride; monoglycerides; glycerol; and water.

The composition may potentially be refined or purified by methods known in the art such as distillation (including flash evaporation, stripping, and deodorization); phase separation; extraction; and drying. The purpose of such refining could be to remove or recover one or more of the above mentioned components from the composition. Examples include, but are not limited to, drying for the removal of water; phase separation for the removal of glycerol; and distillation for the isolation of FAAE. Hence, the crude reactant mixture (composition) can be applied without further refining, or refined by one or more methods. This may comprise separating the phase comprising the FAAE from the glycerol-water phase and further processing the phase with an immobilized lipase to increase the FAAE content. Preferably the FAAE content is increased to least 90%, at least 91%, at least 92%, at least 93%, at least 94%, at least 95%, at least 96%, at least 97%, at least 98%, or even at least 99° A) (w/w).

The present invention is further described by the following examples that should not be construed as limiting the scope of the invention.

Materials and Methods

Lipolytic Activity

The lipolytic activity may be determined using tributyrine as substrate. This method is based on the hydrolysis of tributyrin by the enzyme, and the alkali consumption to keep pH constant during hydrolysis is registered as a function of time.

One Lipase Unit (LU) is defined as the amount of enzyme which, under standard conditions (i.e. at 30° C.; pH 7.0; with 0.1% w/v Gum Arabic as emulsifier and 0.16 M tributyrine as substrate) liberates 1 micromol titrable butyric acid per minute. One KLU is 1000 LU.

Lipolytic Enzymes

Lipase A is a liquid lipase preparation comprising a lipase from *T. lanuginosus* (amino acid sequence shown in positions 1-269 of Sequence Number 2 of WO 95/22615) and having a declared activity of 100 KLU/g and an approximate density of 1.05 g/ml.

Lipase B is a liquid lipase preparation comprising lipase B from *Candida Antarctica* (amino acid sequence shown in Sequence Number 1 in WO 2008/065060) and having a declared activity of 50 KLU/g and an approximate density of 1.20 g/ml.

Lipase C is a liquid lipase preparation comprising a variant of the *T. lanuginosus* lipase having the substitutions T231 R +N233R. The variant is disclosed in WO 2000/60063. The preparation has a declared activity of 100 KLU/g Example 1

Fatty acid methyl esters (FAME) were produced by transesterification of soybean oil with Lipase A using different glycerol-water to triglyceride ratios and different ratios of water in the glycerol-water phase. The following parameters were varied in the experiment setup (see table 1).

TABLE 1

Glycerol-water phase in % of reactant mixture and % of water in the glycerol-water phase tested.

| Glycerol-water phase, % | 20 | 30 | 40 |
|---|---|---|---|
| Amount of water in the glycerol-water phase, % | 0 | 50 | 100 |

TABLE 2

The 9 treatments comprised oil, glycerol, water, methanol and enzyme according to the scheme below.

| | Oil (g) | Glycerol (g) | Water (g) | Methanol (g) | Enzyme dosage (ml) |
|---|---|---|---|---|---|
| 1 | 8 | 0 | 2 | 1.30 | 0.04 |
| 2 | 8 | 1 | 1 | 1.30 | 0.04 |
| 3 | 8 | 2 | 0 | 1.30 | 0.04 |
| 4 | 7 | 0 | 3 | 1.14 | 0.035 |
| 5 | 7 | 1.5 | 1.5 | 1.14 | 0.035 |
| 6 | 7 | 3 | 0 | 1.14 | 0.035 |
| 7 | 6 | 0 | 4 | 0.98 | 0.030 |
| 8 | 6 | 2 | 2 | 0.98 | 0.030 |
| 9 | 6 | 4 | 0 | 0.98 | 0.030 |

Glass reactors (20 ml volume) with glass filter bottom were used. The glass filter was wetted with a small amount of oil before the enzyme was added.

Methanol dosage was 1.5 molar equivalents to the total fatty acids, corresponding to 1.63 g methanol per 10 g oil. The methanol was added as 0.25 equivalents from start, 0.25 equivalents after 2 hours and 1 equivalent after 4 hours.

The reaction was carried out in an Innova incubator at 35° C. and 200 rpm. Reaction time per batch was 24 hours.

After 24 hours the glycerol-water phase containing the enzyme was collected and reused with a new batch of oil and methanol. Five batches were processed with the same enzyme loading. Yield of fatty acid methyl esters was quantified by gas chromatography.

TABLE 3

Yield as total FAME from five batches, in % (w/w) of max. theoretical obtainable yield.

| % water in glycerol-water phase* | Glycerol-water phase, %* | | |
|---|---|---|---|
| | 20 | 30 | 40 |
| 100 | 80.2 | 80.6 | 80.7 |
| 50 | 81.1 | 83.9 | 85.4 |
| 0 | 0.9 | 1.7 | 1.5 |

*At start of 1$^{st}$ batch.

The highest yield expressed as total FAME from five batches was achieved with a 50:50 glycerol-water phase and a glycerol-water phase of 40% (w/w) of the reactant mixture.

Example 2

Fatty acid ethyl esters (FAEE) were produced by transesterification of soybean oil. Soybean oil, glycerol and water in the ratio 8:1:1 (800 g:100 g:100 g) were added to the reactor with an enzyme dosage of 5 g Lipase A/kg oil. The reactor was incubated at 35° C. and stirring at 1000 rpm. Ethanol (96%) in a total dosage of 1.3 molar equivalents to the total fatty acids (168.9 g) was added continuously over the first 5 hours and 25 minutes.

Samples of 1 ml were drawn at 1, 2, 3, 4, 5, 6, 23, and 32 hours and evaporated in a vacuum concentrator at 60° C. for 1½ hour to eliminate excess ethanol. Yield of fatty acid ethyl esters was quantified by gas chromatography. The results are shown in table 4.

TABLE 4

FAEE (ethyl esters) and FFA (free fatty acids) over time as % in the fatty phase.

| Time, hours | FAEE, % | FFA, % |
|---|---|---|
| 1 | 13.3 | 17.5 |
| 2 | 16.4 | 13.0 |
| 5 | 37.9 | 7.7 |
| 22 | 62.6 | 7.7 |
| 32 | 73.9 | 7.3 |
| 50 | 88.5 | 7.4 |

Example 3

Water:glycerol:soybean oil was mixed in the ratio 1:1:8 (2 g:2 g:16 g) or 0.5:1.5:8 (1 g:3 g:16 g) and reacted with lipase (Lipase B) in an amount of 0.5% w/w of oil at 35° C. for 48 hours. Methanol, 1.5 molar equivalents to the total fatty acids was added with 0.25 molar equivalents from start and after 1 hour, the rest after 3 hours. The results are shown in table 5.

TABLE 5

Analysis of FFA and FAME after 48 hours.

| Water:glycerol (%) | FFA (%) | FAME (%) |
|---|---|---|
| 50:50 | 3.5 | 93.8 |
| 25:75 | 2.2 | 95.9 |

The high addition of glycerol (b-set of data) resulted in lower FFA and a high production of FAME. A higher percentage of FAME was achieved for the high glycerol addition. This is surprising considering that glycerol is a reaction product from the transesterification and it would be expected to reduce the FAME formation by pushing the equilibrium of the reaction towards triglyceride formation.

Example 4

Rapeseed oil (85 g) was mixed with a glycerol-water phase consisting of different proportions of water and glycerol; the content of glycerol varying from 0 to 90% w/w of the glycerol-water phase. The amount of glycerol-water phase in the system before each batch was held constant at 20% w/w of the total mass. The enzyme (Lipase C) was added in an amount of 1% w/w of oil. Methanol, 1.5 molar equivalents to the total fatty acids, was added in three equal portions at start, after 2 hours and after 4 hours. Reaction temperature was 35° C. and reaction time was 21 hours. The reaction was carried out in a well mixed batch reactor. The content of FAME and FFA in the fatty phase was determined by GC and titration, respectively, after evaporation of residual methanol.

The results show that substituting parts of the water with glycerol increases the production of FAME and reduces the amount of FFA (table 6).

TABLE 6

Testing different compositions of the glycerol-water phase.

| % glycerol in glycerol-water phase | FAME, % of fatty phase | FFA, % of fatty phase |
|---|---|---|
| 0 | 90.4 | 9.5 |
| 50 | 94.2 | 4.9 |
| 80 | 97.6 | 1.7 |
| 90 | 97.0 | 1.2 |

Example 5

Rapeseed oil (85 g) was used as substrate and mixed with a glycerol-water phase consisting of water for the first batch. The amount of glycerol-water phase in the system for the first batch was 20 w/w % of the total mass. Methanol (1.5 molar equivalents to the fatty acids) was added in three equal portions at start, after 2 hours and after 4 hours. Reaction temperature was 35° C. and the enzyme (Lipase C) dosage was 1% w/w of oil. The reaction was carried out for 24 hrs/batch in a well mixed batch reactor. After each batch the phases were separated by centrifugation and the glycerol-water phase removed. The glycerol-water phase contained the water, the glycerol produced from the transesterification, the enzyme, and approximately 90% of the residual methanol. The remaining 10% of the residual methanol was dissolved in the fatty phase. When re-using the glycerol-water phase the residual methanol was taken into account when adding methanol for the next batch, so for batch 2-5 only 1.0 molar equivalent methanol was added. The content of FAME in oil phase was determined by GC after evaporation of the residual methanol. The results after each batch are shown in table 7.

TABLE 7

Re-use of the glycerol-water phase comprising the enzyme.

| Batch no | FAME, % of fatty phase | FFA, % of fatty phase |
|---|---|---|
| 1 | 91.1 | 8.8 |
| 2 | 89.0 | 9.8 |
| 3 | 88.4 | 8.9 |
| 4 | 87.3 | 8.4 |
| 5 | 87.5 | 7.2 |

The results illustrate that reuse of the glycerol-water phase maintains a very large fraction of the enzyme activity as the FAME content is still very high after batch 5.

For each processed batch the composition of the glycerol-water phase changed due to the amount of glycerol formed in the transesterification process. The glycerol-water phase will be added approximately 85 g*0.1=8.5 g glycerol per batch (28.6% of the glycerol-water phase after the first batch). The calculated proportion of water and glycerol in the glycerol-water phase before each of batches 2-5 are shown in table 8.

TABLE 8

Proportion of glycerol and water of the glycerol-water phase.

| Before batch | Glycerol, % | Water, % |
|---|---|---|
| 2 | 28.6 | 73.4 |
| 3 | 44.4 | 55.6 |
| 4 | 54.5 | 45.5 |
| 5 | 61.5 | 38.8 |

Example 6

Soybean oil and oleic acid in a ratio of 95:5 w/w were used as substrate in transesterification with methanol. Enzyme (Lipase C) dosage was 1% w/w relative to the oil substrate. The glycerol-water phase (glycerol-water phase) consisting of water and glycerol in a ratio of 1:4 w/w was mixed with the substrate in a ratio of glycerol-water phase: substrate=20:80 w/w. Methanol was added in an amount of 1.5 molar equivalents to the total amount of fatty acids. One third of the methanol was added from the start and the remaining methanol at constant rate over the following 4 hours. Reaction temperature was 35° C. and the reaction time was 16 hours. The fatty phase and glycerol-water phase were separated after centrifugation. The fatty phase was washed at 80° C. with 2% w/w of a caustic solution (15 g NaOH in 85 g water) under agitation for 30 minutes. The soap formed in the caustic wash was removed by centrifugation and separation. Samples of the fatty phase before and after caustic wash were analyzed. The results are shown in table 9.

TABLE 9

Composition of fatty phase after transesterification, and after caustic wash. (%)

|  | FAME | FFA | TG | DG | MG |
|---|---|---|---|---|---|
| After transesterification | 95.51 | 2.00 | 0.282 | 0.103 | 0.925 |
| After caustic wash | 98.04 | 0 | 0.132 | 0.167 | 0.266 |

The invention claimed is:

1. A process for production of fatty acid alkyl esters comprising,
   forming a two phase reactant mixture comprising a fatty acid feedstock, an alcohol, water, and glycerol,
   contacting said reactant mixture with one or more lipases, wherein a glycerol-water phase constitutes from 5 to 50% of said reactant mixture (w/w), and wherein glycerol constitutes 30 to 85% of said glycerol-water phase (w/w),
   thereby producing said fatty acid alkyl esters.

2. The process of claim 1, wherein said glycerol-water phase constitutes from 20 to 40% of said reactant mixture.

3. The process of claim 1, wherein glycerol constitutes 30 to 70% of said glycerol-water phrase (w/w).

4. The process of claim 1, wherein glycerol constitutes 40 to 70% of said glycerol-water phase (w/w).

5. The process of claim 1, wherein glycerol constitutes 45 to 70% of said glycerol-water phase (w/w).

6. The process of claim 1, wherein said alcohol is a C1-C5 alcohol.

7. The process of claim 1, wherein said alcohol is ethanol or methanol.

8. The process of claim 1, wherein an alcohol content is less than 4 molar equivalents to an amount of fatty acids in said reactant mixture (free and glyceride bound fatty acids).

9. The process of claim 1, wherein said alcohol is added stepwise and/or continuously.

10. The process of claim 1, further comprising contacting said reactant mixture with a phospholipase, a cutinase, or a mixture thereof.

11. The process of claim 1, wherein said fatty acid feedstock is derived from one or more of algae oil, canola oil, coconut oil, castor oil, coconut oil copra oil, corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, oil from halophytes, animal fat, tallow from pigs, tallow from beef and sheep, lard, chicken fat, fish oil, yellow grease, brown grease, or any combination thereof.

12. The process of claim 1, wherein said process is a batch mode process or a continuous mode process.

13. The process of claim 1, wherein said glycerol-water phase is recovered and re-used.

14. The process of claim 13, wherein an amount of glycerol in said recovered glycerol-water phase or at least a part thereof is reduced before said glycerol-water phrase is re-used.

15. The process of claim 1, wherein solution phases in said reactant mixture are mixed using a high shear mixer or cavitator.

16. The process of claim 1, wherein said process is conducted in a counter-current mode.

17. The process of claim 1, wherein a phase comprising said fatty acid alkyl esters are separated from said glycerol-water phrase and further treated with an immobilized lipase to increase the fatty acid alkyl esters content to at least 90% (w/w).

18. The process of claim 1, wherein a phase comprising said fatty acid alkyl esters is treated with an alkaline agent to facilitate the isolation of a fraction containing said free fatty acid.

19. The process of claim 18, wherein said fraction containing said free fatty acid is a raw material subjected to an esterification process.

20. The process of claim 1, wherein said lipase is from *Candida antarctica*, *Thermomyces lanuginosus*, *Hyphozyma* species, *Rhizomucro miehei*, *Fusarium oxysporum*, *Aspergillus niger*, or *Aspergillus oryzae*.

* * * * *